United States Patent
Osada et al.

(10) Patent No.: US 9,616,202 B2
(45) Date of Patent: Apr. 11, 2017

(54) SELF-EXPANDING INTERPOSED MEMBER SPACING PROTECTIVE SLEEVE FROM RESTENOSIS RESTRAINING AGENT COATED BALLOON CATHETER

(71) Applicant: Terumo Kabushiki Kaisha, Tokyo (JP)

(72) Inventors: Toshihiko Osada, Ashigarakami-gun (JP); Yasushi Kinoshita, Ashigarakami-gun (JP); Hiroaki Kasukawa, Ashigarakami-gun (JP); Keiko Yamashita, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/063,576

(22) Filed: Oct. 25, 2013

(65) Prior Publication Data

US 2014/0052104 A1 Feb. 20, 2014

Related U.S. Application Data

(63) Continuation of application No. PCT/JP2012/064567, filed on Jun. 6, 2012.

(30) Foreign Application Priority Data

Jul. 25, 2011 (JP) ................................ 2011-161480

(51) Int. Cl.
*A61M 25/10* (2013.01)
*A61M 25/09* (2006.01)
*A61M 25/01* (2006.01)

(52) U.S. Cl.
CPC ...... *A61M 25/1002* (2013.01); *A61M 25/104* (2013.01); *A61M 2025/0183* (2013.01);
(Continued)

(58) Field of Classification Search
CPC ........ A61M 29/00; A61M 31/00; A61M 7/12; A61M 2025/105; A61M 2025/1081; A61F 2/82
(Continued)

(56) References Cited

U.S. PATENT DOCUMENTS 4,116,201 A * 9/1978 Shah ......................... 128/207.15
4,219,026 A * 8/1980 Layton ........................... 606/192
(Continued)

FOREIGN PATENT DOCUMENTS

JP       2001-514936 A   9/2001
WO       WO 99/08729 A1  2/1999
(Continued)

OTHER PUBLICATIONS

International Search Report (PCT/ISA/210) mailed on Jul. 10, 2012, by the Japanese Patent Office as the International Searching Authority for International Application No. PCT/JP2012/064567.

*Primary Examiner* — Andrew Gilbert
*Assistant Examiner* — Matthew A Engel
(74) *Attorney, Agent, or Firm* — Buchanan Ingersoll & Rooney PC

(57) ABSTRACT

A treatment device includes: a balloon; a biologically active agent part applied on an outer surface of the balloon; a protective sleeve encircling the balloon and being displaceable proximally; and an interposed member having a self-expanding function arranged between the balloon and the protective sleeve. When the protective sleeve is moved proximally in order for the balloon to be exposed to the inside of a blood vessel, the presence of the interposed member prevents the biologically active agent part from being scraped and peeled off by the inner surface of the protective sleeve.

19 Claims, 6 Drawing Sheets

(52) U.S. Cl.
CPC ............. *A61M 2025/09125* (2013.01); *A61M 2025/105* (2013.01); *A61M 2025/1081* (2013.01)

(58) Field of Classification Search
USPC .............. 604/96.01, 97.01–97.03, 22, 890.1, 604/101.02
See application file for complete search history.

(56) References Cited

U.S. PATENT DOCUMENTS

| | | | |
|---|---|---|---|
| 4,338,942 A * | 7/1982 | Fogarty | 606/194 |
| 4,447,227 A * | 5/1984 | Kotsanis | 604/95.03 |
| 4,744,366 A * | 5/1988 | Jang | 606/194 |
| 4,994,033 A * | 2/1991 | Shockey et al. | 604/101.02 |
| 5,049,132 A * | 9/1991 | Shaffer et al. | 604/101.02 |
| 5,180,367 A * | 1/1993 | Kontos et al. | 604/101.04 |
| 5,213,576 A * | 5/1993 | Abiuso et al. | 604/101.01 |
| 5,256,144 A * | 10/1993 | Kraus et al. | 604/96.01 |
| 5,257,974 A * | 11/1993 | Cox | 604/103.05 |
| 5,304,121 A * | 4/1994 | Sahatjian | 604/509 |
| 5,304,135 A * | 4/1994 | Shonk | 604/103.11 |
| 5,320,605 A * | 6/1994 | Sahota | 604/101.01 |
| 5,342,305 A * | 8/1994 | Shonk | 604/101.02 |
| 5,370,614 A * | 12/1994 | Amundson et al. | 604/103.02 |
| 5,378,237 A * | 1/1995 | Boussignac et al. | 604/103.01 |
| 5,395,311 A * | 3/1995 | Andrews | 604/22 |
| 5,399,165 A * | 3/1995 | Paul, Jr. | 604/95.04 |
| 5,411,016 A * | 5/1995 | Kume et al. | 600/114 |
| 5,447,497 A * | 9/1995 | Sogard et al. | 604/101.02 |
| 5,464,395 A * | 11/1995 | Faxon et al. | 604/103.02 |
| 5,474,530 A * | 12/1995 | Passafaro et al. | 604/22 |
| 5,498,238 A * | 3/1996 | Shapland et al. | 604/501 |
| 5,536,252 A * | 7/1996 | Imran et al. | 604/101.02 |
| 5,556,383 A * | 9/1996 | Wang et al. | 604/103.11 |
| 5,562,620 A * | 10/1996 | Klein et al. | 604/103.01 |
| 5,571,086 A * | 11/1996 | Kaplan et al. | 604/96.01 |
| 5,611,775 A * | 3/1997 | Machold et al. | 604/509 |
| 5,624,411 A * | 4/1997 | Tuch | 604/265 |
| 5,628,730 A * | 5/1997 | Shapland et al. | 604/21 |
| 5,685,847 A * | 11/1997 | Barry | 604/96.01 |
| 5,795,331 A * | 8/1998 | Cragg et al. | 604/103.01 |
| 5,823,996 A * | 10/1998 | Sparks | 604/103.01 |
| 5,857,998 A * | 1/1999 | Barry | 604/103.03 |
| 5,947,985 A * | 9/1999 | Imran | 606/159 |
| 5,976,107 A * | 11/1999 | Mertens et al. | 604/164.13 |
| 6,136,011 A * | 10/2000 | Stambaugh | 606/159 |
| 6,156,053 A * | 12/2000 | Gandhi et al. | 606/194 |
| 6,176,871 B1 * | 1/2001 | Pathak et al. | 623/1.21 |
| 6,210,356 B1 * | 4/2001 | Anderson et al. | 604/22 |
| 6,319,227 B1 * | 11/2001 | Mansouri-Ruiz | 604/95.01 |
| 6,443,926 B1 * | 9/2002 | Kletschka | 604/96.01 |
| 6,471,672 B1 * | 10/2002 | Brown et al. | 604/101.01 |
| 6,485,500 B1 * | 11/2002 | Kokish et al. | 606/194 |
| 6,500,146 B1 * | 12/2002 | Pinchuk et al. | 604/96.01 |
| 6,706,013 B1 * | 3/2004 | Bhat et al. | 604/96.01 |
| 6,733,474 B2 * | 5/2004 | Kusleika | 604/103.01 |
| 6,945,957 B2 * | 9/2005 | Freyman | 604/96.01 |
| 7,052,510 B1 * | 5/2006 | Richter | 623/1.11 |
| 7,220,252 B2 * | 5/2007 | Shah | 604/500 |
| 8,034,022 B2 * | 10/2011 | Boatman | 604/96.01 |
| 2002/0143294 A1 * | 10/2002 | Duchon et al. | 604/131 |
| 2002/0161377 A1 * | 10/2002 | Rabkin | A61F 2/95 606/108 |
| 2004/0064093 A1 * | 4/2004 | Hektner et al. | 604/103.01 |
| 2006/0129180 A1 * | 6/2006 | Tsugita | A61F 2/013 606/200 |
| 2006/0235506 A1 * | 10/2006 | Ta | A61F 2/91 623/1.16 |
| 2006/0259119 A1 * | 11/2006 | Rucker | A61F 2/82 623/1.11 |
| 2006/0259132 A1 * | 11/2006 | Schaffer | A61F 2/82 623/1.49 |
| 2008/0300571 A1 * | 12/2008 | LePivert | 604/503 |
| 2009/0005733 A1 * | 1/2009 | Chiu et al. | 604/99.01 |
| 2009/0105686 A1 * | 4/2009 | Snow | A61F 2/958 604/509 |
| 2009/0306582 A1 * | 12/2009 | Granada et al. | 604/22 |
| 2010/0228333 A1 | 9/2010 | Drasler et al. | |
| 2010/0324483 A1 * | 12/2010 | Rozenberg et al. | 604/98.01 |
| 2011/0054443 A1 | 3/2011 | Weber | |
| 2011/0060276 A1 * | 3/2011 | Schaeffer et al. | 604/101.05 |
| 2014/0039358 A1 * | 2/2014 | Zhou et al. | 601/3 |

FOREIGN PATENT DOCUMENTS

WO    WO 2009/150099 A1    12/2009
WO    WO 2012/009409 A1 *    1/2012

* cited by examiner

SELF-EXPANDING INTERPOSED MEMBER SPACING PROTECTIVE SLEEVE FROM RESTENOSIS RESTRAINING AGENT COATED BALLOON CATHETER

CROSS REFERENCES TO RELATED APPLICATIONS

This application is a continuation of International Application No. PCT/JP2012/064567 filed on Jun. 6, 2012, and claims priority to Japanese Application No. 2011-161480 filed on Jul. 25, 2011, the entire content of both of which is incorporated herein by reference.

TECHNICAL FIELD

The present invention generally relates to a treatment device for performing a predetermined treatment by delivering its distal portion to a lesion part in a lumen of a living body.

BACKGROUND DISCUSSION

In treatment of cardiac infarction or stenocardia, for example, a method of forcing open a lesion part (stenosed part) of a coronary artery by a balloon catheter is practiced. Improvements of stenosed parts formed in such biorgans as other blood vessels, bile duct, trachea, esophagus, urethra, nasal cavity and other organs may also be performed in the same or similar manner. A balloon catheter is, in general, configured to have an elongated shaft and a balloon which is disposed at a distal portion of the shaft and is inflated radially. With a preceding guide wire inserted and passed in the balloon catheter, the balloon catheter is sent to the stenosed part in the body.

In such a treatment method, in order to prevent stenosis that causes stenosis again after the treatment of the stenosed part, it has been proposed in recent years to coat the outer surface of the balloon with a drug having a restenosis-preventing effect. On the other hand, in order to prevent the drug on the balloon from being peeled off due to frictional contact (mutual rubbing) between the drug and a blood vessel inner wall during delivery of the balloon to the stenosed part, consideration has been given to providing a sheath as a protective cover for covering the balloon. An example is disclosed in Japanese Application Publication No. 2001-514936 (JP-T-2001-514936).

When a sheath configured as described in Japanese Application Publication No. 2001-514936 is adopted as the protective cover for covering the drug applied on the balloon, a problem that arises involves peeling of the drug off the outer surface of the balloon due to rubbing of the inner circumferential surface of the sheath and the drug against each other at the time of retracting the sheath.

SUMMARY

A treatment device according to one aspect includes a device body having a shaft; an inflatable balloon disposed at a distal portion of the shaft; a biologically active agent part on the outer surface of the balloon and containing at least one biologically active agent; a protective sleeve covering the biologically active agent part and displaceable proximally in relation to the device body; an interposed member having a self-expanding function and disposed between the balloon and the protective sleeve in surrounding relation to the balloon and displaceable proximally in relation to the device body; and wherein the interposed member expands, while still surrounding the balloon, when the protective sleeve is displaced proximally.

In the treatment device configured as above, the biologically active agent part applied on the outer surface of the balloon is covered with the protective sleeve. This helps ensure that contact between the inner wall of a body lumen and the biologically active agent part can be prevented or restrained from occurring during delivery of the balloon to the lesion part, and, therefore, peeling of the biologically active agent part is inhibited or prevented. In addition, the arrangement of the interposed member between the protective sleeve and the balloon helps prevent the biologically active agent part, applied on the outer surface of the balloon, and the inner surface of the protective sleeve from making contact with each other. Therefore, at the time of moving the protective sleeve proximally so as to expose the balloon, the biologically active agent part can be inhibited or prevented from being scraped and peeled off by the protective sleeve. Furthermore, when the protective sleeve is moved proximally, the interposed member automatically expands by its self-expanding function. Therefore, when the interposed member is thereafter moved proximally, the biologically active agent part is not scraped and peeled off by the interposed member.

According to another aspect, a treatment device positionable in a blood vessel to treat a stenosed region comprises: an elongated shaft possessing a distal portion; an inflatable balloon fixed to the distal portion of the shaft so that the balloon and the shaft move together; a flow path inside the shaft that communicates with the interior of the balloon and through which fluid is introduced into the interior of the balloon to inflate and outwardly expand the balloon; a restenosis-restraining biologically active agent on the outer surface of the balloon that restrains restenosis, with the restenosis-restraining biologically active agent being applied to the stenosed region of the blood vessel when the balloon is inflated and outwardly expanded into contact with the stenosed region; a protective sleeve covering the entire axial extent of the biologically active agent, with the protective sleeve possessing an inner surface and being axially movable in a proximal direction relative to the elongated shaft; and a cylindrically shaped interposed member positioned radially between the protective sleeve and the restenosis-restraining biologically active agent to space the protective sleeve from the restenosis-restraining biologically active agent and prevent the restenosis-restraining biologically active agent from contacting the protective sleeve, wherein the interposed member possesses a self-expanding function in which the interposed member expands radially outwardly when the protective sleeve is axially moved in the proximal direction relative to the interposed member.

In the treatment device as above, preferably, an operating mechanism extending along the shaft at least to a proximal end side of the device body is disposed at a proximal end of the interposed member, and the operating mechanism is so configured as to inhibit the interposed member from being moved proximally at the time of moving the protective sleeve proximally, and to displace the interposed member proximally by an operation on the proximal end side of the device body. This helps ensure that the interposed member can be securely inhibited from being moved attendantly on the proximal movement of the protective sleeve, and that an operation of moving the interposed member proximally can be relatively easily carried out on the operator's side. Thus, excellent operability is realized.

The operating mechanism in the treatment device can include a linear member arranged along the shaft, whereby flexibility of the treatment device can be secured, which is preferable.

The treatment device can include a fixing mechanism by which the operating mechanism is detachably fixed to the device body, and so the interposed member can be rather assuredly disposed between the protective sheath and the balloon until the fixation is intentionally released.

The fixing mechanism can be disposed at a proximal portion of the device body so that the fixation of the operating mechanism by the fixing mechanism can be relatively easily released. Thus, excellent operability is realized.

The fixing mechanism can be configured to include a first clamping part disposed on the device body side, and a second clamping part which is engageable and disengageable in relation to the device body, and the operating mechanism is fixed by clamping of the operating mechanism between the first clamping part and the second clamping part. This helps ensure that the fixation and the release of the fixation can be carried out rather assuredly and easily.

The interposed member and the operating mechanism can be integrally composed of the same member so that a reduced number of component parts and a simplified configuration can be realized.

The operating mechanism can be in the shape of a tube extending along the shaft to a proximal portion of the shaft, and so movement of the interposed member associated with proximal movement of the protective sleeve can be inhibited more assuredly.

It is possible to carry out a treating method that involves disposing a balloon of a treatment device, in which an interposed member having a self-expanding function is disposed between the balloon coated on its outer surface with a biologically active agent part containing at least one biologically active agent and a protective sleeve encircling the balloon, at a lesion part which is a target part to be treated in a body lumen; moving the protective sleeve proximally and expanding the interposed member while maintaining a state in which the interposed member is disposed outside of the balloon; moving the expanded interposed member proximally to a position retracted from a position just outside of the balloon; and inflating the balloon to force open the lesion part from inside and adhering at least part of the biologically active agent part to the lesion part.

According to another aspect of the disclosure here, a method comprises: inserting a distal portion of a treatment device into a blood vessel having a lesion part, wherein the treatment device comprises: a shaft; an inflatable balloon at a distal portion of the shaft; a restenosis-restraining biologically active agent on the outer surface of the balloon that restrains restenosis, a protective sleeve covering the restenosis-restraining biologically active agent and possessing an inner surface; and a self-expanding interposed member between the balloon and the protective sleeve in surrounding relation to the balloon. The method further involves forwardly moving the treatment device in the blood vessel to position the balloon at the lesion part, proximally moving the protective sleeve relative to the interposed member and the balloon while the self-expanding interposed member continues to cover the restenosis-restraining biologically active agent so that the interposed member prevents the restenosis-restraining biologically active agent from contacting the inner surface of the moving protective sleeve, with the protective sleeve being proximally moved to expose at least a portion of the interposed member; proximally moving the interposed member relative to the balloon, after proximally moving the protective sleeve, to expose the balloon and the restenosis-restraining biologically active agent on the balloon; and inflating the balloon to press the restenosis-restraining biologically active agent on the balloon against the lesion part to dilate the lesion part in the blood vessel and so that the restenosis-restraining biologically active agent adheres to the dilated lesion part.

DETAILED DESCRIPTION

Figure 1:
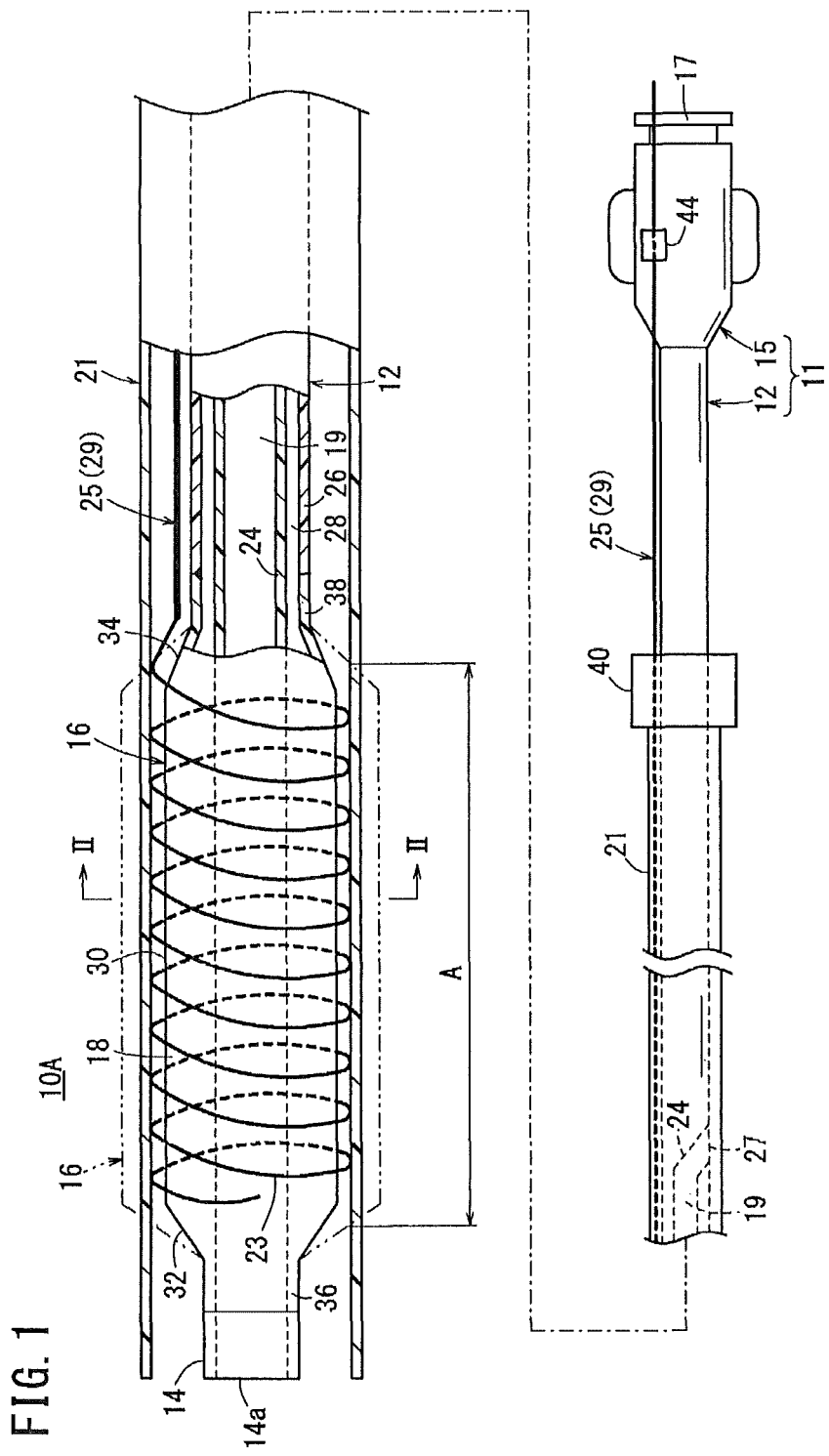
FIG. 1 is a partial longitudinal cross-sectional view of a treatment device according to a first embodiment disclosed by way of example.

Set forth below, with reference to the drawing figures, is a detailed description of embodiments of the treatment device disclosed here by way of example.

Reference is initially made to FIG. 1 which illustrates the treatment device 10A according to one embodiment. For ease in illustration and understanding, part of the distal portion of the treatment device 10A is shown in section, and an intermediate portion of the treatment device is omitted. The distal portion of the treatment device 10A is shown on the upper side in FIG. 1, while a proximal portion of the treatment device 10A is shown on the lower side in FIG. 1. In addition, the distal portion of the treatment device 10A is shown in an enlarged form as compared with the proximal portion.

The treatment device 10A is a device used to apply a predetermined treatment to a lesion part in a body lumen (blood vessel or the like), with the distal portion of the treatment device delivered to the lesion part. In the present embodiment, the treatment device 10A is configured as a so-called PTCA (Percutaneous Transluminal Coronary Angioplasty) balloon catheter such that a balloon 16 disposed at the distal portion of the treatment device is inflated at a stenosed part (as a lesion part) so as to force open the stenosed part from inside, thereby achieving treatment. The treatment device is applicable not only to such PTCA balloon catheters but also to catheters for improvements of lesion parts formed in such biorgans as other blood vessels, bile duct, trachea, esophagus, urethra, nasal cavity and the like organs.

As shown in FIG. 1, the treatment device 10A includes: a small-diameter, elongated shaft 12; a hub 15 disposed on the proximal end of the shaft 12; a tip 14 secured to the distalmost end of the shaft 12; the balloon 16 disposed in the vicinity of a distal portion of the shaft 12 on the proximal end of the tip 14; a biologically active agent part 18 formed on the outer surface of the balloon 16 by coating; a protective sleeve 21 covering the biologically active agent part 18; an interposed member 23 disposed between the balloon 16 and the protective sleeve 21; and an operating mechanism 25 disposed on the proximal end of the interposed member 23.

The shaft 12 and the hub 15 constitute a device body 11. The shaft 12 is a double tube including an inner tube 24 possessing a lumen 19 in which to insert and pass (convey) a guide wire, and an outer tube 26 disposed in surrounding relation to the inner tube 24. The shaft 12 is a part which constitutes a main body (catheter tube) of the treatment device 10A.

Figure 3:
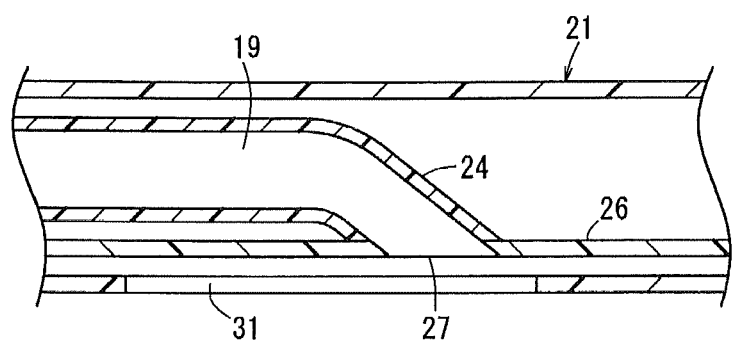
FIG. 3 is an enlarged longitudinal cross-sectional view of a part of the treatment device shown in FIG. 1.

The inner tube 24 extends within the balloon 16 and the outer tube 26, and its proximal end is bent and is joined, in a liquid-tight manner, to an opening part 27 formed in a longitudinally intermediate portion of the outer tube 26 as illustrated in FIGS. 1 and 3. Accordingly, this treatment device 10A is configured as a "rapid exchange type" catheter in which a guide wire inserted via a distal opening 14a of the tip 14 is inserted and extends in the lumen 19 of the inner tube 24 from the distal side toward the proximal side and is extends out from the opening part 27.

The treatment device 10A may also be configured as an "over-the-wire type" catheter in which an opening for a guide wire is formed in the hub 15 on the proximal end of the shaft 12.

The outer tube 26 is a flexible tubular member extending in the axial direction so as to interconnect the rear end of the balloon 16 and the distal end of the hub 15. A lumen extends axially throughout the outer tube 26. The inner tube 24 protrudes from the distal end of the outer tube 26. A gap exists between the inner tube 24 and the outer tube 26. This gap 28 extends in the axial direction, possesses a hollow cylindrical shape and communicates with the inside of the balloon 16. The gap 28 functions as a flow path for supplying a fluid for inflating the balloon 16.

The hub 15 has a balloon inflation port 17. The balloon inflation port 17 communicates with the gap 28 via lumens of the hub 15 and the outer tube 26. The material constituting the hub 15 is not particularly limited, and may be a comparatively hard resin material, examples of which include polyvinyl chloride, polyethylene, polypropylene, cyclic polyolefins, polystyrene, poly(4-methylpentene-1), polycarbonate, acrylic resins, acrylonitrile-butadiene-styrene copolymer, polyesters such as polyethylene terephthalate, polyethylene naphthalate, etc., butadiene-styrene copolymer, and polyamides (e.g., nylon 6, nylon 6,6, nylon 6,10, nylon 12).

The balloon inflation port 17 is configured to permit inflation fluid supply means such as an indeflator to be connected to the balloon inflation port 17. With the inflation fluid supply means connected to the balloon inflation port 17 and with the inflation fluid supply means operated, an inflation fluid (e.g., a contrast agent) can be fed from the inflation fluid supply means into the balloon 16 through the hub 15 and the lumen (inclusive of the above-mentioned gap 28) inside the outer tube 26.

The inner tube 24 is a tube which has, for example, an outside diameter of about 0.1 to 1.0 mm, preferably about 0.3 to 0.7 mm, a wall thickness of about 10 to 150 µm, preferably about 20 to 100 µm, and a length of about 100 to 2000 mm, preferably about 150 to 1500 mm. The outside diameter and the inside diameter of the inner tube 24 may each be different between the distal side and the proximal side. That is, the inside diameter and the outside diameter of the inner tube 24 at the distal side of the inner tube 24 may differ from the inside diameter and the outside diameter of the inner tube 24 at the proximal side of the inner tube 24.

The outer tube 26 is a tube which has, for example, an outside diameter of about 0.3 to 3.0 mm, preferably about 0.5 to 1.5 mm, a wall thickness of about 10 to 150 µm, preferably about 20 to 100 µm, and a length of about 300 to 2000 mm, preferably about 700 to 1600 mm. The outside diameter and the inside diameter of the outer tube 26 may each be different between the distal side and the proximal side.

The inner tube 24 and the outer tube 26 are preferably structured (configured) to have appropriate flexibility and appropriate rigidity, in order that an operator can relatively smoothly insert and pass (convey) the elongated shaft 12 into a body lumen such as a blood vessel while gripping and operating a proximal portion. From this point of view, the inner tube 24 and the outer tube 26 are preferably formed, for example, of a polymer material such as polyolefin (e.g., polyethylene, polypropylene, polybutene, ethylene-propylene copolymer, ethylene-vinyl acetate copolymer, ionomers, or mixtures of two or more of them), polyvinyl chloride, polyamides, polyamide elastomers, polyurethane, polyurethane elastomers, polyimides, and fluoro-resins or their mixtures, or composed of a multilayer tube of two or more of the above-mentioned polymer materials.

The balloon 16 is so configured that it can be folded (contracted) and inflated according to variations in the internal pressure. In FIG. 1, the balloon 16 in a contracted state is shown in solid lines, while the balloon 16 in an inflated state is shown in imaginary lines (two-dot chain lines). The balloon 16 includes a cylindrical section (straight section) 30 to be inflated into a tubular (cylindrical) shape by an inflation fluid injected into the inside thereof, a distal tapered section 32 gradually reduced in outer diameter on the distal side of the cylindrical section 30, and a proximal tapered section 34 gradually reduced in outer diameter on the proximal side of the cylindrical section 30.

The balloon 16 also includes a cylindrical distal-side non-inflation section 36 disposed on the distal end of the distal tapered section 32 and joined to the outer circumferential surface of the inner tube 24 in a liquid-tight manner, and a cylindrical proximal-side non-inflation section 38 disposed on the proximal end of the proximal tapered section 34 and joined to the distal portion of the outer tube 26 in a liquid-tight manner, whereby the balloon 16 is secured to the shaft 12. The inside diameter of the distal-side non-inflation section 36 is approximately equal to the outside diameter of the inner tube 24, while the outside diameter of the proximal-side non-inflation section 38 is approximately equal to the outside diameter of the outer tube 26. It suffices for the balloon 16 to be secured to the inner tube 24 and the outer tube 26 in a liquid-tight manner; thus, the securing is achieved, for example, by adhesion or heat sealing (fusing).

As for the size of the balloon 16 in its inflated state, for example, the outside diameter of the cylindrical section 30 is about 1 to 10 mm, preferably about 1 to 7 mm, and the length is about 5 to 350 mm, preferably about 5 to 300 mm. In addition, the distal-side non-inflation section 36 has an outside diameter of about 0.5 to 1.5 mm, preferably about 0.6 to 1.3 mm, being approximately equal to the outside diameter of the tip 14, and a length of about 1 to 5 mm, preferably about 1 to 2 mm. The proximal-side non-inflation section 38 has an outside diameter of about 0.5 to 1.6 mm, preferably about 0.7 to 1.5 mm, and a length of about 1 to 5 mm, preferably about 2 to 4 mm. Furthermore, the length of each of the distal tapered section 32 and the proximal tapered section 34 is about 1 to 10 mm, preferably about 3 to 7 mm.

The balloon 16 as above has to have appropriate flexibility, like the inner tube 24 and the outer tube 26, and has to have sufficient strength as to be able to securely force open a stenosed part. The material of the balloon 16 may be the same as, or different from, the material constituting the inner tube 24 and the outer tube 26 of which examples have been set forth above.

The tip 14 is a relatively short tube having an outside diameter approximately equal to the outside diameter of the distal-side non-inflation section 36 of the balloon 16, and an inside diameter approximately equal to the outside diameter of the inner tube 24. The length of the tip 14 in the axial direction is about 0.5 to 10 mm, for example. The tip 14 is joined to a distal portion of the inner tube 24 in a liquid-tight manner by external fitting, protrudes distally beyond a distal opening of the lumen 19, and has a proximal end face joined to a distal end face of the distal-side non-inflation section 36 of the balloon 16. The distal opening 14a of the tip 14 communicates with the lumen 19 of the inner tube 24, and serves as an entrance for the guide wire.

The tip 14 has its material and size appropriately set so as to be configured at least more flexible than the inner tube 24 or the outer tube 26. The tip 14 is preferably formed, for example, of a polymer material such as polyolefin (e.g., polyethylene, polypropylene, polybutene, ethylene-propylene copolymer, ethylene-vinyl acetate copolymer, ionomers, or mixtures of two or more of them), polyvinyl chloride, polyamides, polyamide elastomers, polyurethane, polyurethane elastomers, polyimides, and fluoro-resins or their mixtures, or composed of a multilayer tube of two or more of the above-mentioned polymer materials.

The tip 14 as above is a part which flexibly advances through curved parts, rugged parts and the like within a body lumen as the distalmost end of the treatment device 10A, penetrates a stenosed part (lesion part), and guides smooth insertion and passage of the treatment device 10A. The tip 14 may be omitted. In that case, it is preferable to adopt a configuration in which the distalmost end position of the inner tube 24 and the distalmost end position of the distal-side non-inflation section 36 of the balloon 16 coincide with each other, or a configuration in which the distalmost end position of the inner tube 24 protrudes slightly beyond the distalmost end position of the distal-side non-inflation section 36.

Figure 2:
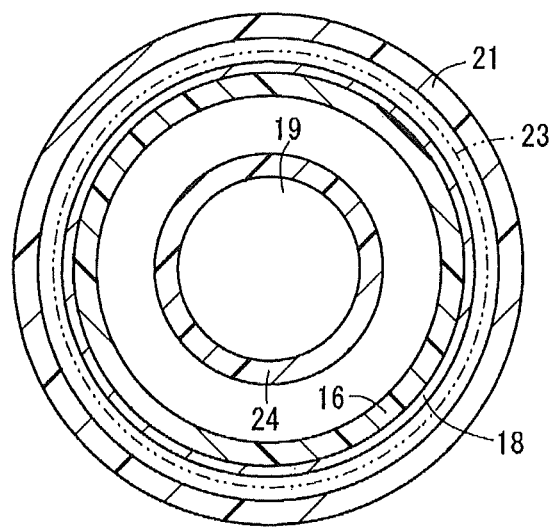
FIG. 2 is a cross-sectional view taken along line the section line II-II of FIG. 1.

Referring to FIG. 2, the biologically active agent part 18 applied on the outer surface of the balloon 16 contains at least one biologically active agent. Specifically, for securing the adhesion (placement) of the biologically active agent part 18 onto a lesion part (stenosed part), the biologically active agent part 18 is preferably applied to the outer circumferential surface of the balloon 16 over the whole circumferential extent of the balloon (i.e., covering an angular range of 360 degrees) and over at least the entire axial length or extent of the cylindrical section 30. Therefore, the biologically active agent part 18 is preferably applied, for example, over the axial range or extent denoted by A in FIG. 1 (the range from an intermediate portion of the distal tapered section 32 to an intermediate portion of the proximal tapered section 34).

The thickness (coating thickness) of the biologically active agent part 18 is preferably 3 to 100 μm, more preferably 5 to 50 μm. The biologically active agent part 18 may be formed on the whole part of the outer surface of the balloon 16, or may be formed on part of the outer surface of the balloon 16.

The biologically active agent contained in the biologically active agent part 18 is not specifically restricted so long as it is effective in restraining restenosis when adhered to a treated stenosed part in a body lumen. Specific examples of the biologically active agent include carcinostatic agents, immunosuppressants, antibiotics, antirheumatics, antithrombogenic drugs, antihyperlipidemic drugs, ACE inhibitors, calcium antagonists, integrin inhibitors, antiallergic agents, antioxidants, GPIIbIIIa antagonists, retinoids, flavonoids, carotenoids, lipid improving drugs, DNA synthesis inhibitors, tyrosine kinase inhibitors, antiplatelet drugs, vascular smooth muscle proliferation inhibitors, antiinflammatory agents, bio-derived materials, interferon, and NO production promoting substances.

More specific and preferable examples of the carcinostatic agents include vincristine sulfate, vinblastine sulfate, vindesine sulfate, irinotecan hydrochloride, paclitaxel, docetaxel hydrate, methotrexate, and cyclophosphamide. More specific and preferable examples of the immunosuppressants include sirolimus, tacrolimus hydrate, azathioprine, ciclosporin, mycophenolate mofetil, gusperimus hydrochloride, and mizoribin.

More specific and preferable examples of the antibiotics include mitomycin C, doxorubicin hydrochloride, actinomycin D, daunorubicin hydrochloride, idarubicin hydrochloride, pirarubicin hydrochloride, aclarubicin hydrochloride, epirubicin hydrochloride, peplomycin sulfate, and zinostatin stimalamer. More specific and preferable examples of the antirheumatics include sodium aurothiomalate, penicillamine, and lobenzarit disodium. More specific and preferable examples of the antithrombogenic drugs include heparin, ticlopidine hydrochloride, and hirudin.

More specific and preferable examples of the antihyperlipidemic drugs include HMG-CoA reductase inhibitors, and probucol. Besides, more specific and preferable examples of the HMG-CoA reductase inhibitors include cerivastatin sodium, atorvastatin, nisvastatin, pitavastatin, fluvastatin sodium, simvastatin, lovastatin, and pravastatin sodium.

More specific and preferable examples of the ACE inhibitors include quinapril hydrochloride, perindopril erbumine, trandolapril, cilazapril, temocapril hydrochloride, delapril hydrochloride, enalapril maleate, lisinopril, and captopril. More specific and preferable examples of the calcium antagonists include nifedipine, nilvadipine, diltiazem hydrochloride, benidipine hydrochloride, and nisoldipine. More specific and preferable examples of the antiallergic agents include tranilast.

More specific and preferable examples of the retinoids include all-trans-retinoic acid. More specific and preferable examples of the antioxidants include catechins, anthocyanin, proanthocyanidin, lycopene, and β-carotene. Particularly preferred among the catechins is epigallocatechin gallate. More specific and preferable examples of the tyrosine kinase inhibitors include genistein, tyrphostin, and erbstatin. More specific and preferable examples of the antiinflammatory agents include steroids such as dexamethasone, prednisolone, etc. and aspirin.

More specific and preferable examples of the bio-derived materials include EGF (epidermal growth factor), VEGF (vascular endothelial growth factor), HGF (hepatocyte growth factor), PDGF (platelet derived growth factor), and BFGF (basic fibroblast growth factor).

The biologically active agent part 18 may contain only one of the above-mentioned biologically active agents, or may contain two or more different ones of the biologically active agents. In the case where the biologically active agent part 18 contains two or more biologically active agents, the combination of them may be appropriately selected, as necessary, from among the above-mentioned biologically active agents.

The protective sleeve 21 is an elongated flexible tubular member which surrounds the shaft 12. The protective sleeve 21 covers the biologically active agent part 18, and extends along the shaft 12 to a proximal portion of the shaft 12. For instance, the protective sleeve 21 is so configured as to cover at least the whole part (the entire axial extent) of the biologically active agent part 18, which is formed on a part or the whole part of the balloon 16. The protective sleeve 21 can be displaced (slid) proximally in relation to the device body 11. The protective sleeve 21 can be retracted to such a position that the distance between the distal end of the protective sleeve 21 and the proximal end of the balloon 16 becomes not less than the axial length of the interposed member 23.

In an initial state, the distal end (distalmost end) of the protective sleeve 21 is located on the distal side relative to the distal end (distalmost end) of the biologically active agent part 18 applied on the outer surface of the balloon 16. In other words, in the initial state, the biologically active agent part 18 is entirely covered by the protective sleeve 21, so that the biologically active agent part 18 does not make contact with any member outside of the protective sleeve 21. Accordingly, the biologically active agent part 18 applied on the outer surface of the balloon 16 is protected appropriately.

As shown in FIG. 3, the protective sleeve 21 is provided with a slot 31 through which to lead out the guide wire inserted and extending in the lumen 19, the slot 31 being formed along the axial direction of the protective sleeve 21. The position and range (including size or length) of the slot 31 are such that the opening part 27 formed in a side surface of the shaft 12 so as to lead out the guide wire therethrough is exposed to the exterior, irrespective of the location of the protective sleeve 21 within its movable range.

The material constituting the protective sleeve 21 is not specifically restricted; for example, at least one material selected from among those set forth above as examples of the material for the inner tube 24 and the outer tube 26 can be adopted. Desirably, the protective sleeve 21 has such strength as to be able to hold the interposed member 23 (described later) in a compressed state, and has an inner surface with lubricity for the interposed member 23. This helps ensure that when the protective sleeve 21 is slid proximally, the frictional resistance due to the interposed member 23 can be suppressed to a relatively low level.

As shown in FIG. 1, a hub 40 is disposed at the proximal end of the protective sleeve 21. The hub 40 has a hollow shape (hollow cylindrical shape) in which the shaft 12 is inserted and passed. In order that the operator's operation of gripping by fingers and pulling proximally can be relatively easily carried out, the hub 40 has an appropriate length and has an appropriate outside diameter greater than the outside diameter of the protective sleeve 21. By gripping the hub 40 with fingers, the operator can rather easily perform an operation of sliding or axially moving the protective sleeve 21.

The interposed member 23 possesses a hollow cylindrical overall shape, and has a self-expanding function or self-expanding characteristics. That is, the interposed member 23 is configured to automatically expand radially outwardly, absent any applied force, when the protective sleeve 21 is moved proximally so as to no longer cover the interposed member 23. In the state of being disposed between the balloon 16 and the protective sleeve 21, the interposed member 23 is in a contracted state because it is inhibited by the inner surface of the protective sleeve 21 from expanding outwardly. When released from the protective sleeve 21, on the other hand, the interposed member 23 elastically expands (becomes larger in diameter) by its self-expanding function or characteristics. The interposed member 23 is disposed inside the protective sleeve 21 and on the outside of the biologically active agent part 18 (radially between the inner surface of the protective sleeve 21 and the outer surface of the biologically active agent part 18), for the purpose of preventing the biologically active agent part 18 from making contact with the inner surface of the protective sleeve 21. That is, the interposed member 23 spaces the biologically active agent part 18 (entire biologically active agent part 18) from the inner surface of the protective sleeve 21. Therefore, it is preferable that the axial length of the interposed member 23 is at least equal to or greater than the coating range (axial extent) of the biologically active agent part 18 (the range denoted by A in FIG. 1).

The interposed member 23 in the configuration example shown in the drawings possesses a coil shape obtained by spirally winding an elastic wire or fiber. But the interposed member 23 is not limited in this regard. For example, the interposed member 23 may be configured to have a tubular overall shape with a meshed structure obtained by weaving elastic wires or fibers, to have a tubular overall shape in which a plurality of rings formed from an elastic wire or fiber are interconnected, or to have a tubular overall shape in which a plurality of ring-like cells bent in a Z-shape or S-shape are interconnected.

The material for forming the interposed member 23 is not specifically restricted insofar as it can impart a self-expanding function or self-expanding characteristics to the interposed member 23. Superelastic alloys (shape memory alloys) and shape memory resins can be adopted. Examples of the superelastic alloys include Ti—Ni alloys, Ti—Ni—Fe alloys, Cu—Zn alloys, Cu—Zn—Al alloys, Cu—Al—Ni alloys, Cu—Au—Zn alloys, Cu—Sn alloys, Ni—Al alloys, Ag—Cd alloys, Au—Cd alloys, In—Ti alloys, and In—Cd alloys. Besides, metals and alloys having ordinary elasticity, such as stainless steels, tantalum and cobalt alloys can be adopted as the material for forming the interposed member 23.

On the proximal end of the interposed member 23 is disposed the operating mechanism 25. In the present embodiment, the operating mechanism 25 is composed of a linear member 29. The linear member 29 is positioned and passed between the protective sleeve 21 and the shaft 12, and is arranged along the shaft 12. The distal end of the linear member 29 is connected to the proximal end of the interposed member 23, while the proximal end of the linear member 29 protrudes proximally from the gap between the protective sleeve 21 and the shaft 12, to be led out to the exterior. That is, as shown in FIG. 1, the linear operating member 29 extends proximally beyond the proximal-most end of the protective sleeve 21.

This linear member 29 is a member for inhibiting proximal movement of the interposed member 23 at the time of moving the protective sleeve 21 proximally, and for displacing the interposed member 23 proximally by being operated on the proximal end side of the device body 11. For this purpose, the thickness (outside diameter) and material of the linear member 29 are configured so that the linear member 29 has appropriate rigidity so as not to be bent significantly when a proximal load is exerted on the linear member 29 from the interposed member 23.

The material constituting the linear member 29 may be selected, for example, from among those mentioned above as examples of the material for the interposed member 23. In this case, the interposed member 23 and the linear member 29 may be formed from the same material, or may be formed from different materials. In the case where the interposed member 23 and the linear member 29 are formed from the same material, both of them may be integrally configured as a single member. This can help contribute to a reduced number of component parts and a simplified configuration.

Figure 4A:
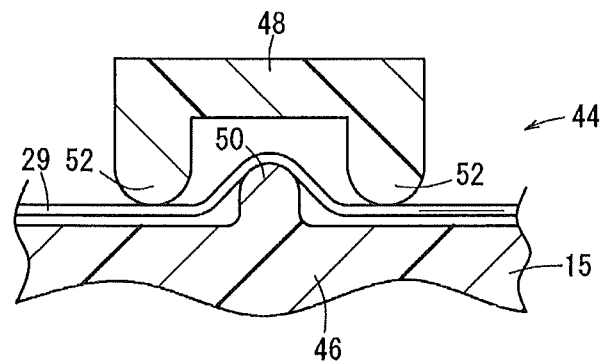
FIG. 4A is an enlarged cross-sectional view of a fixing mechanism in a locked state.
Figure 4B:
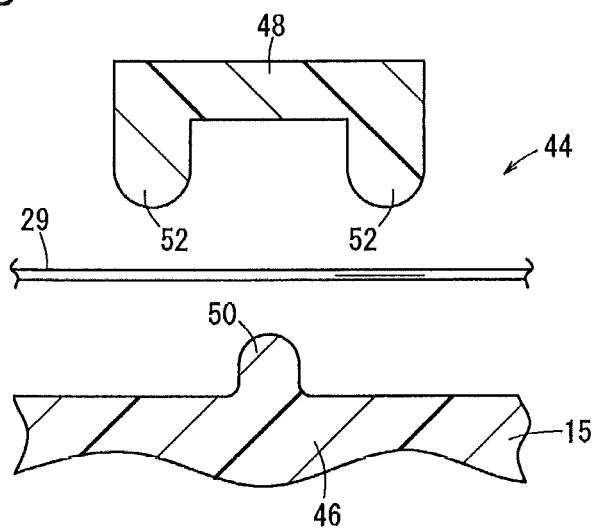
FIG. 4B is an enlarged cross-sectional view of the fixing mechanism in an unlocked state.

As shown in FIG. 1, the treatment device 10A has a fixing mechanism 44 by which the linear member 29 as the operating mechanism 25 is fixed to the device body 11 in a detachable manner. The fixing mechanism 44 in the example shown in the drawing is disposed at a proximal portion of the device body 11, specifically, on the hub 15. As shown in FIGS. 4A and 4B, the fixing mechanism 44 includes a first clamping part 46 disposed on the hub 15, and a second clamping part 48 which can be engaged and disengaged in relation to the first clamping part 46. The first clamping part 46 is formed with a first projection 50. The second clamping part 48 is formed with two second projections 52 spaced from each other.

When the linear member 29 is clamped between the first clamping part 46 and the second clamping part 48, as shown in FIG. 4A, the linear member 29 is held in a bent state by the first projection 50 and the second projections 52, resulting in a state in which the linear member 29 is inhibited from moving (locked state). On the other hand, when the second clamping part 48 is disengaged from the first clamping part 46, as shown in FIG. 4B, the linear member 29 is released from the clamping between the first clamping part 46 and the second clamping part 48, resulting in a state in which the linear member 29 is permitted to move (unlocked state).

In order to permit the operator to relatively easily grip the linear member 29 by fingers and pull it proximally at the time of pulling the linear member 29, a grip section greater in diameter than the linear member 29 may be disposed at the proximal end of the linear member 29.

The fixing mechanism 44 is not restricted to the configuration in which the linear member 29 is clamped between the first clamping part 46 and the second clamping part 48. Other configurations which operate or function to detachably fix the linear member 29 to the device body 11 may be adopted. Examples of other configurations of the fixing mechanism 44 include adhesion, heat sealing (fusing), physical engagement or a combination of them can be adopted. In this case, the strength of fixation by the adhesion, heat sealing (fusing) or physical engagement is set to such a level that the fixation between the linear member 29 and the device body 11 is released by an operator's operation of pulling the linear member 29.

The treatment device 10A according to the present embodiment is configured as above-described. Now, the operation and effect of the treatment device 10A will be described below.

In the case of treatment of a stenosed part generated in a coronary artery or the like by use of the treatment device 10A, first, the form of the stenosed part as a lesion part is determined by intravascular imaging or intravascular ultrasound diagnosis. Next, the guide wire is precedingly introduced into a blood vessel percutaneously from a femoral part or the like by Seldinger technique, for example. In addition, the guide wire is inserted and passed in the lumen 19 of the inner tube 24 via the distal opening 14a of the tip 14, and the treatment device 10A is inserted into the blood vessel.

Then, the guide wire is radioscopically advanced to the target lesion part (stenosed part) and is advanced past the lesion part to be set indwelling there, and the treatment device 10A is advanced along the guide wire into the blood vessel (for example, into the coronary artery). In the case of the treatment device 10A according to the present embodiment, the biologically active agent part 18 applied on the outer surface of the balloon 16 is covered with the protective sleeve 21. Therefore, during delivery of the balloon 16 to the lesion part, contact between the blood vessel inner wall and the biologically active agent part 18 can be prevented or restrained from occurring. Consequently, peeling of the biologically active agent part 18 can be effectively prevented.

Figure 5A:
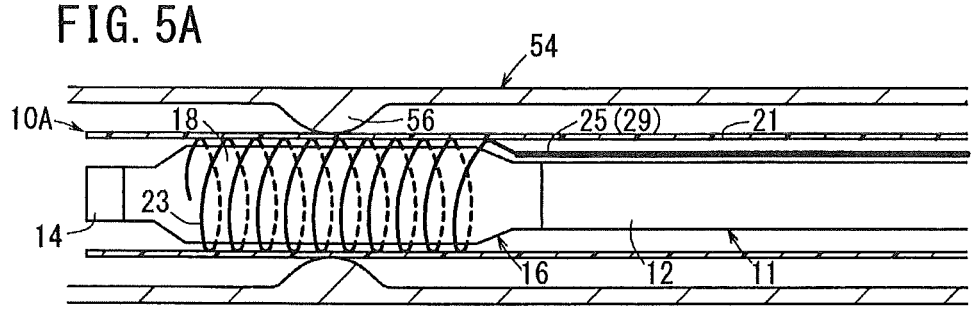
FIG. 5A is a partial longitudinal cross-sectional view of a first state illustrating an operational aspect of the treatment device shown in FIG. 1.

When the treatment device 10A is advanced within a blood vessel 54, as shown in FIG. 5A, the tip 14 at the distal end of the treatment device 10A soon passes (penetrates) through a lesion part (stenosed part) 56, and the balloon 16 encircled by the protective sleeve 21 is disposed at the lesion part 56 (the balloon 16 is positioned in axially overlapping relationship to the stenosed or lesion part 56).

Figure 5B:
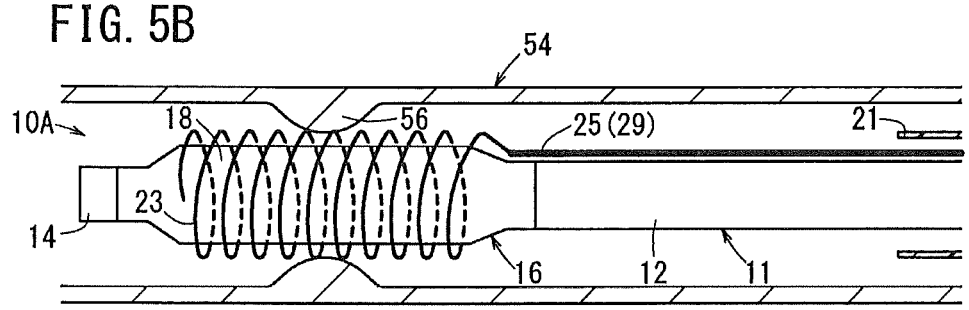
FIG. 5B is a partial longitudinal cross-sectional view of a second state illustrating another operational aspect of the treatment device shown in FIG. 1.

When the balloon 16 is thus disposed at the lesion part 56, the protective sleeve 21 is pulled proximally to expose the balloon 16 and the interposed member 23 to the inside of the blood vessel 54, as shown in FIG. 5B. In this case, the interposed member 23 is fixed by the fixing mechanism 44 through the linear member 29. Even when the protective sleeve 21 is moved proximally, therefore, the movement would not be attended by a proximal movement of the interposed member 23. Thus, the interposed member 23 remains held in a position of surrounding the balloon 16, and expands by its self-expanding function. In the treatment device 10A shown in FIG. 5B, an appropriate gap (annular gap) is formed between the interposed member 23 and the biologically active agent part 18. In addition, desirably, the outside diameter of the interposed member 23 in a natural state (expanded state) is greater than the inside diameter of the protective sleeve 21 and is smaller than the inside diameter of the relevant blood vessel 54.

Even if the interposed member 23 and the biologically active agent part 18 are in contact with each other in the state before the expansion of the interposed member 23, the expansion of the interposed member 23 involves an increase in the diameter of the interposed member 23. In this instance, the interposed member 23 parts from the surface of the biologically active agent part 18 in a direction perpendicular to the surface. Therefore, the biologically active agent part 18 is not very susceptible to being scraped off by the interposed member 23.

Next, the fixation of the linear member 29 and the device body 11 to each other by the fixing mechanism 44 is released. In the case of the present embodiment, specifically, the first clamping part 46 is disengaged from the second clamping part 48, whereby a proximal portion of the linear member 29 is released from the fixing mechanism 44. In the case where the fixing mechanism 44 is configured by adhesion, heat sealing (fusing) or the like, the fixation is released by pulling a proximal portion of the linear member 29.

Figure 5C:
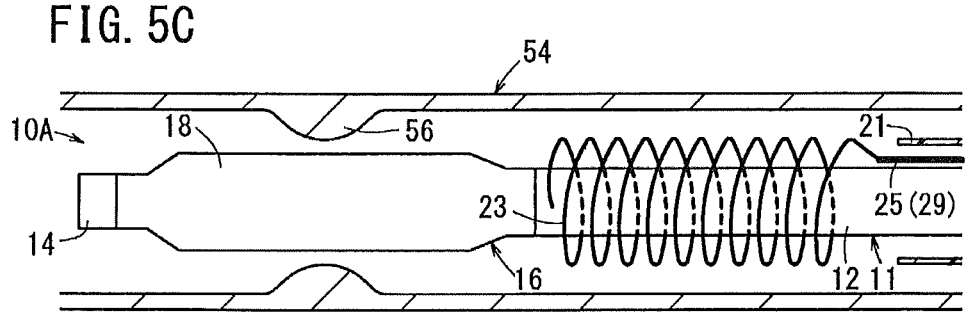
FIG. 5C is a partial longitudinal cross-sectional view of a third state illustrating an additional operational aspect of the treatment device shown in FIG. 1.

When the fixation of the linear member 29 by the fixing mechanism 44 is released, the linear member 29 is pulled proximally (relative to the shaft 12 and balloon 16), whereby the interposed member 23 is moved proximally to be retracted from the position of encircling the balloon 16, as shown in FIG. 5C. In this case, an appropriate gap is present between the interposed member 23 and the biologically active agent part 18. This helps ensure that when the interposed member 23 is moved proximally, the biologically active agent part 18 applied on the outer surface of the balloon 16 is inhibited or prevented from being scraped and peeled off by the interposed member 23. The retraction of the interposed member 23 from the position just outside the balloon 16 results in the biologically active agent part 18 being thoroughly exposed to the inside of the blood vessel 54.

Figure 5D:
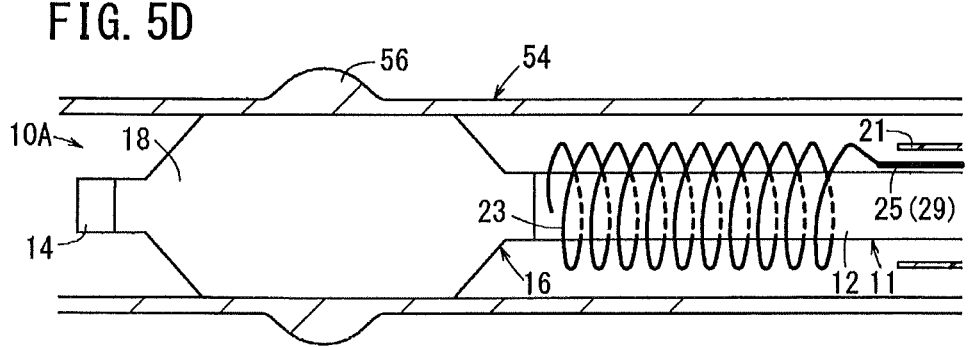
FIG. 5D is a partial longitudinal cross-sectional view of a fourth state illustrating a further operational aspect of the treatment device shown in FIG. 1.

After the biologically active agent part 18 is exposed to the inside of the blood vessel 54, the balloon 16 is inflated under the action of the inflation fluid supply means to force open the lesion part 56 from the inside, whereby the diameter of the blood vessel portion where the lesion part 56 has been generated is brought closer to a normal blood vessel diameter (see FIG. 5D). In this instance, the biologically active agent part 18 on the outer surface of the balloon 16 is pressed against the dilated lesion part 56, to be adhered to the lesion part 56. As above-mentioned, the biologically active agent part 18 contains the biologically active agent having an effect of restraining restenosis. Therefore, restenosis of the treated part can be restrained.

Meanwhile, if the biologically active agent part 18 on the balloon 16 was covered directly with an axially movable sleeve, peeling of the biologically active agent part 18 can be inhibited or prevented until the balloon 16 reaches the lesion part 56. However, unlike in the above-described present embodiment, when the sleeve is thereafter shifted proximally for the purpose of exposing the biologically active agent part 18, the biologically active agent part 18 is scraped and peeled off by the sleeve.

On the other hand, in the treatment device 10A according to the present embodiment, the arrangement of the interposed member 23 between the protective sleeve 21 and the balloon 16 inhibits or prevents the biologically active agent part 18 on the outer surface of the balloon 16 from making contact with the inner surface of the protective sleeve 21. When the protective sleeve 21 is moved proximally to expose the balloon 16, therefore, the biologically active agent part 18 can be prevented from being scraped and peeled off by the protective sleeve 21. When the protective sleeve 21 is retracted from the position of encircling the balloon 16, the interposed member 23 automatically expands by its self-expanding function. This helps ensure that when the interposed member 23 is thereafter moved proximally, the biologically active agent part 18 is not scraped and peeled off.

In addition, in the case of the present embodiment, the operating mechanism 25 (the linear member 29) is so configured as to inhibit proximal movement of the interposed member 23 at the time of moving the protective sleeve 21 proximally, and to displace the interposed member 23 proximally by an operation on the proximal end side of the device body 11. Consequently, a situation in which the interposed member 23 is moved in association with a proximal movement of the protective sleeve 21 can be securely prevented. An operation of moving the interposed member 23 proximally can be rather easily carried out on the operator's side. Thus, excellent operability is ensured.

In the treatment device 10A, furthermore, the fixing mechanism 44 is provided by which the operating mechanism 25 is fixed to the device body 11 in a detachable manner. This helps ensure that the interposed member 23 can be assuredly disposed between the protective sleeve 21 and the balloon 16 until the fixation is intentionally released. Moreover, the fixing mechanism 44 is disposed on the proximal portion of the device body 11. Therefore, the fixation of the linear member 29 by the fixing mechanism 44 can be released rather easily. Thus, excellent operability is promised.

In the case of the present embodiment, the fixing mechanism 44 includes the first clamping part 46 disposed on the side of the device body 11, and the second clamping part 48 which can be engaged and disengaged in relation to the device body 11. When the operating mechanism 25 is clamped between the first clamping part 46 and the second clamping part 48, the operating mechanism 25 is fixed thereby. Accordingly, the fixation of the operating mechanism 25 and the release of the fixation can be carried out relatively assuredly and easily.

Figure 6:
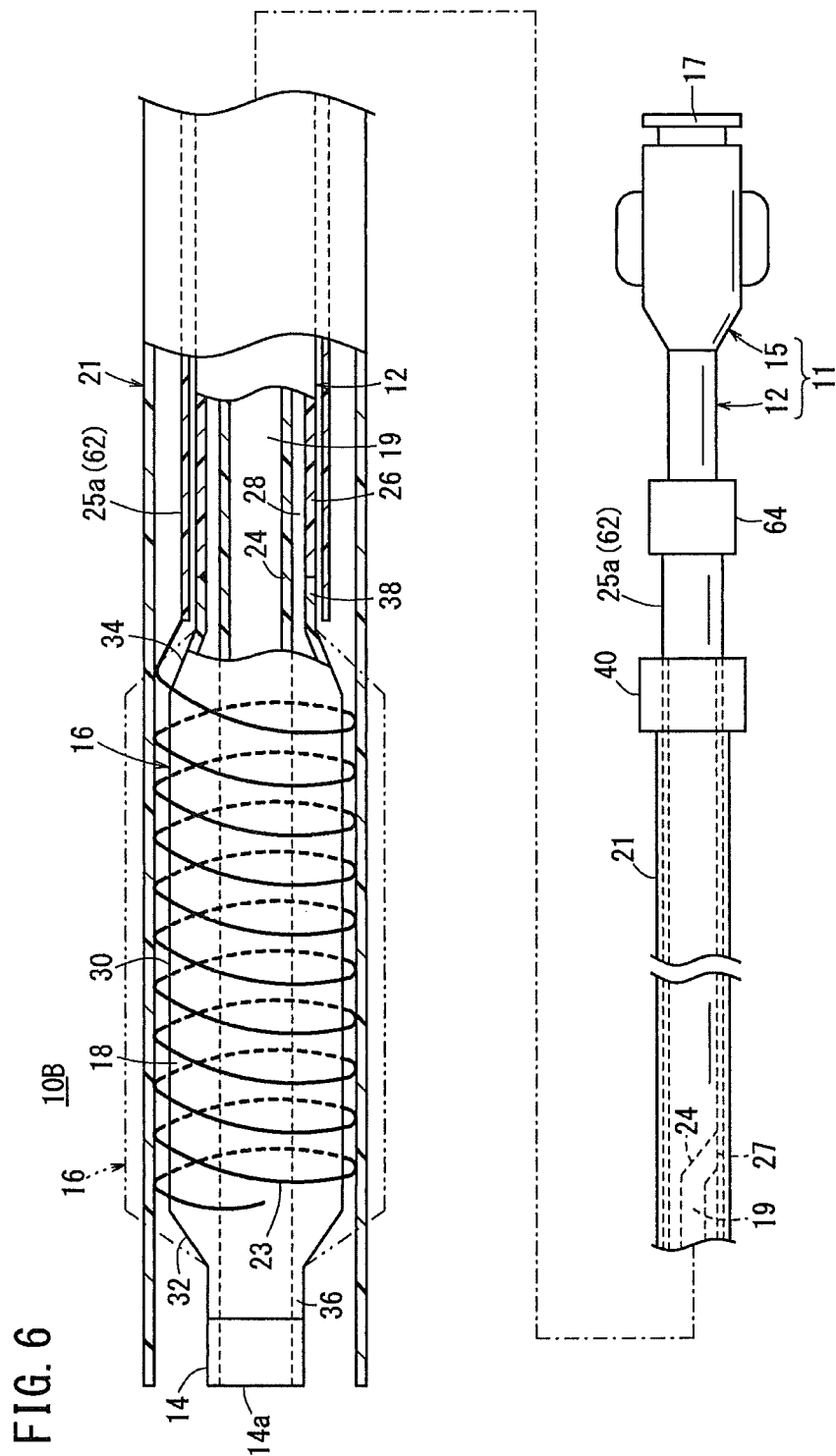
FIG. 6 is a partial longitudinal cross-sectional view of a treatment device according to a second embodiment disclosed as another example.

FIG. 6 illustrates a treatment device 10B according to a second embodiment disclosed here. Components of the treatment device 10B shown in FIG. 6 which are the same as the components of the treatment device 10A shown in FIG. 1 above are denoted by the same reference numerals, and a detailed description of such features is not repeated.

As shown in FIG. 6, an operating mechanism 25a is disposed at the proximal end of an interposed member 23. The operating mechanism 25a includes a traction tube 62 disposed between a shaft 12 and a protective sleeve 21, and a hub 64 disposed at (connected to) the proximal end of the traction tube 62. The traction tube 62 is a flexible, elongated, small-diameter tubular member (cylindrical member), is so disposed as to be axially slidable in relation to the shaft 12, has its distal end connected to the interposed member 23, and has its proximal portion protruding from a hub 40 disposed at the proximal end of the protective sleeve 21.

The traction tube 62 is formed with a slot (a slot similar to the slot 31 shown in FIG. 3) for leading out a guide wire inserted and passed in a lumen 19, the slot being disposed along the axis of the traction tube 62. The position and range of this slot are so set that an opening part 27 formed in a side surface of the shaft 12 for the purpose of leading out a guide wire is exposed to the exterior, irrespectively of the location of the traction tube 62 within its movable range.

The material constituting the traction tube 62 is not specifically restricted. For instance, at least one material selected from among those set forth above as examples of the material for the inner tube 24 and the outer tube 26 can be adopted.

The hub 64 disposed at the proximal end of the traction tube 62 has a hollow shape (hollow cylindrical shape) in which the shaft 12 is positioned and through which the shaft 12 passes. In order that the operator's operation of gripping the hub with fingers and pulling proximally can be relatively easily carried out, the hub 64 has an appropriate length and has an appropriate outside diameter greater than the outside diameter of the traction tube 62.

In order to expand the interposed member 23 on the outside of the balloon 16 like in FIG. 5B by use of the treatment device 10B configured as above, the protective sleeve 21 is slid proximally while holding the position of the traction tube 62 relative to the shaft 12. This makes it possible to retract the protective sleeve 21 from the position just outside of the balloon 16, with the interposed member 23 kept disposed outside of the balloon 16. By this operation, the balloon 16 and the interposed member 23 are exposed to the inside of a blood vessel 54. In the case of the present embodiment, the operating mechanism 25a is configured in a tubular shape extending along the shaft 12 to a proximal portion of the shaft 12, and has higher rigidity as compared with the linear member 29 shown in FIG. 1. Accordingly, a situation in which the interposed member 23 is moved attendantly on (in association with) the proximal movement of the protective sleeve 21 can be prevented more reliably.

Next, the traction tube 62 is slid or moved proximally (relative to the shaft 12 and balloon 16), whereby the interposed member 23 is moved proximally to be retracted from the position of encircling the balloon 16, in the same manner as described above referring to FIG. 5C. Thereafter, in the same manner as described above referring to FIG. 5D, the balloon 16 is inflated under an action of inflation fluid supply means to force open a lesion part 56 from the inside. Consequently, the portion where the lesion part 56 is located or has been generated is brought closer to a normal blood vessel diameter, and a biologically active agent part 18 is adhered to the lesion part 56.

In the second embodiment, other components and aspects of the treatment device that are the same as in the first embodiment exhibit the same or equivalent operations and effects to the operations and effects associated with the common components and aspects in the first embodiment.

In place of the configuration described in the first and second embodiments above, a configuration may be adopted in which, when the protective sleeve 21 is further moved proximally after the protective sleeve 21 is displaced proximally to such a position as to permit the whole part of the interposed member 23 to expand, the interposed member 23 can also be moved proximally together with the protective sleeve 21. As such a configuration, there can be adopted, for example, a configuration in which the protective sleeve 21 and the interposed member 23 are preliminarily interconnected by a linear member or the like having a predetermined slackness, or a configuration in which the interposed member 23 is caught on the protective sleeve 21 when the protective sleeve 21 is retracted to a predetermined position.

The detailed description above describes a treatment device and manner of use or operation disclosed by way of example. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment device comprising:
   a device body having a shaft;
   an inflatable balloon disposed at a distal portion of the shaft, the inflatable balloon possessing an outer surface;
   a biologically active agent on the outer surface of the inflatable balloon and containing at least one biologically active agent;
   a protective sleeve covering the biologically active agent and displaceable proximally in relation to the device body;
   an interposed member having a self-expanding function and disposed between the inflatable balloon and the protective sleeve in surrounding relation to the inflatable balloon, the entirety of the interposed member disposed between the inflatable balloon and the protective sleeve having the self-expanding function, and the interposed member is displaceable proximally in relation to the device body to be completely retracted from the inflatable balloon, so that when the inflatable balloon expands the biologically active agent on the outer surface of the inflatable balloon directly contacts a target site and the inflatable balloon does not contact the interposed member; and
   the interposed member expanding, while still surrounding the inflatable balloon, when the protective sleeve is displaced proximally.

2. The treatment device according to claim 1, further comprising an operating mechanism fixed to a proximal end of the interposed member so that the interposed member moves together with the operating mechanism, the operating mechanism extending along the shaft at least to a proximal end side of the device body, the operating mechanism being configured to inhibit the interposed member from moving proximally relative to the inflatable balloon during proximal displacement of the protective sleeve, and the operating mechanism being configured to displace the interposed member proximally upon operation on the proximal end side of the device body.

3. The treatment device according to claim 2, wherein the interposed member and the operating mechanism are integrally formed so that the interposed member and the operating mechanism constitute a common member.

4. The treatment device according to claim 2, wherein the operating mechanism is a tube extending along the shaft to a proximal portion of the shaft.

5. The treatment device according to claim 2, wherein the operating mechanism includes a linear member extending along the shaft.

6. The treatment device according to claim 5, wherein the operating mechanism is detachably fixed to the device body by a fixing mechanism.

7. The treatment device according to claim 6, wherein the fixing mechanism is disposed at a proximal portion of the device body.

8. The treatment device according to claim 7, wherein the fixing mechanism includes a first clamping part on the device body and a second clamping part configured to engage and be disengaged from the first clamping part, and the operating mechanism is fixed by clamping the operating mechanism between the first clamping part and the second clamping part.

9. A treatment device positionable in a blood vessel of a living body to treat a stenosed region, the treatment device comprising:
   an elongated shaft possessing a distal portion;
   an inflatable balloon fixed to the distal portion of the elongated shaft so that the inflatable balloon and the elongated shaft move together, the inflatable balloon possessing an outer surface and an interior;
   a flow path inside the elongated shaft that communicates with the interior of the inflatable balloon and through which fluid is introduced into the interior of the inflatable balloon to inflate and outwardly expand the inflatable balloon;
   a restenosis-restraining biologically active agent on the outer surface of the inflatable balloon that restrains restenosis, the restenosis-restraining biologically active agent being applied to the stenosed region of the blood vessel when the inflatable balloon is inflated and outwardly expanded into contact with the stenosed region;
   a protective sleeve covering an entirety of the outer surface of the inflatable balloon having the restenosis-restraining biologically active agent, the protective sleeve possessing an inner surface and being axially movable in a proximal direction relative to the elongated shaft;

a cylindrically shaped interposed member positioned radially between the protective sleeve and the restenosis-restraining biologically active agent to space the protective sleeve from the restenosis-restraining biologically active agent and prevent the restenosis-restraining biologically active agent from contacting the protective sleeve both before the treatment device is delivered to the stenosed region and when the treatment device is at the stenosed region, the entirety of the cylindrically shaped interposed member that is positioned radially between the protective sleeve and the restenosis-restraining biologically active agent possessing a self-expanding function in which the cylindrically shaped interposed member expands radially outwardly when the protective sleeve is axially moved in the proximal direction relative to the cylindrically shaped interposed member, and the cylindrically shaped interposed member is configured to be completely retracted from the inflatable balloon to allow the restenosis-restraining biologically active agent on the outer surface of the inflatable balloon to directly contact the stenosed region when the inflatable balloon is expanded; and the cylindrically shaped interposed member and the restenosis-restraining biologically active agent on the outer surface of the inflatable balloon being configured to contact one another when the treatment device is moved in the living body towards the stenosed region while the cylindrically shaped interposed member is positioned radially between the protective sleeve and the restenosis-restraining biologically active agent.

10. The treatment device according to claim 9, wherein the cylindrically shaped interposed member is a wound coil.

11. The treatment device according to claim 9, further comprising a linear operating member fixed to the cylindrically shaped interposed member so that the cylindrically shaped interposed member moves together with the linear operating member, the linear operating member extending proximally along the elongated shaft at least to a proximal end of the elongated shaft.

12. The treatment device according to claim 11, wherein the cylindrically shaped interposed member and the linear operating member are integrally formed so that the cylindrically shaped interposed member and the linear operating member constitute a common member.

13. The treatment device according to claim 11, further comprising a fixing mechanism that detachably fixes the linear operating member relative to the elongated shaft so that the linear operating member is fixed in position relative to the elongated shaft.

14. The treatment device according to claim 13, wherein the fixing mechanism is disposed at a proximal portion of the elongated shaft.

15. The treatment device according to claim 13, wherein the fixing mechanism includes a first clamping part fixed to the elongated shaft and a second clamping part configured to engage and be disengaged from the first clamping part, the linear operating member being fixed relative to the elongated shaft by being clamped between the first clamping part and the second clamping part.

16. The treatment device according to claim 9, further comprising a cylindrical operating member fixed to the cylindrically shaped interposed member so that the cylindrically shaped interposed member moves together with the cylindrical operating member, the cylindrical operating member extending proximally beyond a proximal-most end of the protective sleeve.

17. The treatment device according to claim 16, wherein the cylindrical operating member possesses a proximal end connected to a hub so that axial movement of the hub results in axial movement of the cylindrical operating member, the hub being axially movable relative to the elongated shaft.

18. The treatment device according to claim 16, wherein the cylindrically shaped interposed member and the cylindrical operating member are integrally formed so that the cylindrically shaped interposed member and the cylindrical operating member constitute a common member.

19. The treatment device according to claim 9, wherein the cylindrically shaped interposed member possesses an inner surface spaced from the restenosis-restraining biologically active agent so that an annular gap exists between the inner surface of the cylindrically shaped interposed member and the restenosis-restraining biologically active agent.

* * * * *